(12) United States Patent
Baig et al.

(10) Patent No.: US 10,588,833 B2
(45) Date of Patent: Mar. 17, 2020

(54) METHODS AND COMPOSITIONS TO INCREASE THE HARDNESS AND RESISTANCE OF ENAMEL

(71) Applicant: The Procter & Gamble Company, Cincinnati, OH (US)

(72) Inventors: Arif Ali Baig, Mason, OH (US); Aaron Reed Biesbrock, Maineville, OH (US); Jennifer M. Kennedy, Loveland, OH (US); Samuel James St. John, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/249,936

(22) Filed: Jan. 17, 2019

(65) Prior Publication Data

US 2019/0216693 A1 Jul. 18, 2019

Related U.S. Application Data

(60) Provisional application No. 62/618,137, filed on Jan. 17, 2018.

(51) Int. Cl.
 *A61K 8/21* (2006.01)
 *A61Q 11/00* (2006.01)
 *A61K 8/24* (2006.01)
 *A61K 8/19* (2006.01)

(52) U.S. Cl.
 CPC .................. *A61K 8/21* (2013.01); *A61K 8/19* (2013.01); *A61K 8/24* (2013.01); *A61Q 11/00* (2013.01); *A61K 2800/5922* (2013.01); *A61K 2800/87* (2013.01)

(58) Field of Classification Search
 None
 See application file for complete search history.

(56) References Cited

U.S. PATENT DOCUMENTS

| 4,183,915 | A | * | 1/1980 | Gaffar | A61K 8/21 |
| | | | | | 424/52 |
| 5,605,677 | A | | 2/1997 | Schumann | |
| 6,036,944 | A | * | 3/2000 | Winston | A61K 8/24 |
| | | | | | 424/49 |
| 6,372,198 | B1 | | 4/2002 | Abbate | |
| 2008/0280260 | A1 | * | 11/2008 | Belikov | A46B 11/002 |
| | | | | | 433/215 |

OTHER PUBLICATIONS

Eversole, S. L., Saunders-Burkhardt, K. & Faller, R. V. Erosion prevention potential of an over-the-counter stabilized SnFinf2/inf dentifrice compared to 5000 ppm F prescription-strength products. J. Clin. Dent. 26, 44-49 (2015).
Faller, R.V. et al., "Enamel protection: a comparison of marketed dentifrice performance against dental erosion", Am. J. Dent. 24, 205-210 (2011).
Featherstone, J.D.B. et al., "Comparison of Artificial Caries-Like Lesions by Quantitative Microradiography and Microhardness Profiles", Caries Res. 17, 385-391 (1983).
Fuierer, T. A. et al., "A Mineralization Adsorption and Mobility Study of Hydroxyapatite Surfaces in the Presence of Zinc and Magnesium Ions". Langmuir 10, 4721-4725 (1994).
Ghadimi, E. et al., "Trace elements can influence the physical properties of tooth enamel", Springerplus 2, 499 (2013).
Stephan, R. M. "Intra-Oral Hydrogen-Ion Concentrations Associated With Dental Caries Activity", J. Dent. Res. 23, 257-266 (1944).
Stookey, George K. et al., "The Featherstone laboratory pH cycling model: A prospective, multi-site validation exercise", Am. J. Dent. 24, 322-328 (2011).
Search and Written Opinion for PCT/US2019/013898 dated May 8, 2019.
Bergstrom, David H. et al. "Quantitative Microradiographic Study of Simultaneous Demineralization/Remineralizaation of Dental Enamel in Weak Acid Buffers".
Driessens, F. C. M. et al. "Microradiography and Electron-Microprobe Analysis of Some Caries-Like Lesions of Enamel Prepared In Vitro in Human Teeth", Archs Oral Biol. vol. 31, No. 12, pp. 837-840, 1986.
Jones, Robert S. et al., "Remineralization of in vitro dental caries assessed with polarization-sensitive optical coherence tomography", Journal of Biomedical Optics 11(1), 014016 (Jan./Feb. 2006).
Thuy, Tran THu et al., "Effect of strontium in combination with fluoride on enamel remineralisation in vitro", Archives of Oral Biology 53 (2008) 1017-1022.
Yamazaki, Hajime et al., "Effect of fluoride on artificial caries lesion progression and repair in human enamel: Regulation of mineral deposition and dissolution under in vivo-like conditions", Archives of Oral Biology 52 (2007) 110-120.

* cited by examiner

*Primary Examiner* — Celeste A Roney
(74) *Attorney, Agent, or Firm* — Parker D. McCrary

(57) ABSTRACT

Teeth can be hardened and made more resistant to acid damage if treated with compositions that allow for the remineralization and demineralization of minerals found in teeth. Exchanging ions in hydroxyapatite for fluoride or other metal ions can result in teeth that are more resistant to chemical and physical insults.

16 Claims, 5 Drawing Sheets

| Step | Treatment Regimen | TIME |
|---|---|---|
|  | Rinse |  |
| 1 | Dentifrice Treatment 1 | 1 minute |
|  | Rinse |  |
| 2 | Demineralization | 6 hours |
|  | Rinse |  |
| 3 | Dentifrice Treatment 2 | 1 minute |
|  | Rinse |  |
| 4 | Remineralizing solution | 18 hours (overnight) |

METHODS AND COMPOSITIONS TO INCREASE THE HARDNESS AND RESISTANCE OF ENAMEL

FIELD OF THE INVENTION

The present invention relates to methods and compositions that can exchange ions from the enamel of teeth to increase its resistance to physical and chemical insults exposed to the oral cavity during life of a subject. This invention also relates to methods and compositions that can precipitate particulate coatings on the enamel surface of teeth to increase its resistance to physical and chemical insults exposed to the oral cavity during life of a subject.

BACKGROUND OF THE INVENTION

Tooth enamel has both organic and inorganic phases. The organic phase is composed of proteins, e.g., amelogenin, while the inorganic phase is composed of hydroxyapatite ($Ca_5(PO_4)_3(OH)$ or $Ca_{10}(PO_4)_6(OH)_2$, HAP) and substituted-hydroxyapatite (sHAP). The inorganic phase has ordered, crystalline phases of well-packed HAP crystals with some substitutions of the Ca, $PO_4$, and OH groups with other molecules, such as other metals, fluoride, carbonates, hydrogen phosphates, and chloride. In biological systems, enamel can differ from pure HAP in stoichiometry, composition, crystallinity, and in other physical and mechanical properties. For example, biological apatites are usually calcium deficient and carbonate substituted. Thus, biological apatites can be referred to as carbonate apatite instead of hydroxyapatite (HAP). While, the composition of human enamel and of biological apatites are relatively known, the impact of trace elements on the physical-chemical properties, such as crystallite size, microstrain, hardness, and solubility of human enamel and sHAP is still of interest.

For example, it has been shown that some incorporated trace elements like Ti and Al are correlated with the mechanical and optical properties of naturally occurring human enamel. The incorporation of trace elements into human enamel can occur via biological processes; however, the concentration of these elements in human enamel—by as much as 1000× in some cases—is not well understood. As such, it would be useful to have methods to increase the concentration of certain trace elements in teeth to improve surface hardness, whiteness, and acid resistance of teeth. Compositions and methods for achieving these results have not been identified until now.

Over the course of a lifetime, teeth must resist daily physical insults including those from mechanical process that include chewing (attrition), brushing (abrasion), and bruxing (abfraction). The mechanical durability of a tooth is related to the surface hardness of the tooth, as well as its crack propagation resistance that are related to the trace element composition of the tooth. These properties can be influenced by modifying the chemical properties of human enamel. The benefit of such control would be increased durability of the tooth and longer lifetime of the tooth in situ. However, there have been few attempts to mitigate tooth loss from physical insult by changing the chemical structure of the tooth because the physical wear process, especially physical wear caused by cracking and fatigue failure from repeated loading, is poorly understood. Some processes by which physical insults can lead to mechanical wear include abrasion (loss via three-body wear), attrition (loss via grinding on occlusal surfaces), and abfraction (loss by repeated loading and cracking at the enamel/cementum interface).

Tooth hardness and susceptibility to cracking are both influenced by the crystal size domain along the c-axis in human enamel. Several metal ions have been correlated with enamel c-axis crystal size, including, for example, $Fe^{2+}$, $Zn^{2+}$, $Ti^{4+}$, $Ce^{3+}$, and $Al^{3+}$.

Teeth must also resist daily chemical insults, including multiple cycles per day to conditions where the tooth can be dissolved. In these circumstances, the aqueous environment local to the tooth is undersaturated relative to hydroxyapatite. A shift to undersaturated environment occurs when the pH is lowered from the biological homeostatic pH (roughly 6.5-8) to an acidic pH (roughly less than pH~5 for typical biological levels of Ca and $PO_4$ in saliva). pH in the oral cavity can be lowered by the metabolites of fermentable carbohydrate digestion by the oral cavity bacteria or by the consumption of low pH foods like wine, yogurt, or carbonated beverages. For example, fluoride substitution for hydroxide in human enamel can dramatically reduce the solubility of human enamel, because fluoroapatite (FAP or HAP with OH substituted with F) has a lower critical pH than HAP. Trace metals, when incorporated at the right degree of substitution, can slow the rate of enamel dissolution when exposed to acid. Both metals and fluoride, thusly, reduce the susceptibility of enamel towards dissolution. The chemical durability of a tooth, therefore, is related to the composition of the tooth near the surface. Consequently, the chemical durability, just like the mechanical durability, can be influenced by modifying the chemical properties of human enamel near its surface.

Typically, chemical damage to teeth is repaired through remineralizing without demineralizing teeth. The incorporation of elements to strengthen the tooth post-eruption rely on biological processes that first damage the tooth, which creates atomic vacancies in the apatite of enamel and dentin for the incorporation of fluoride and trace metals.

The additional incorporation of trace metals can further stabilize the apatite lattice of enamel by reducing the solubility of the tooth. Metals that can stabilize the apatites lattice of enamel include, for example, $Mg^{2+}$, $Sr^{2+}$, $Sn^{2+}$, $Ti^{4+}$, $Al^{3+}$, $Zn^{2+}$, $Fe^{2+}$, $Fe^{3+}$, $Mo^{6+}$, $B^{3+}$, $Ba^{2+}$, and/or $In^{3+}$. Additionally, trace metal content in drinking water is associated with a decreased caries rate. Thus, trace metal incorporation into the tooth can help slow acid damage.

Accordingly, there is a need for novel compositions and methods to chemically modify teeth to improve enamel hardness and increase the enamel's resistance to dissolution and acid erosion, without any damage to biological tissues that is typical during remineralization only processes. The present invention provides methods and compositions capable of exchanging ions with the hydroxyapatite mineral component of dental enamel, such that the resulting enamel is harder and more resistant to chemical and physical insult. Additionally, the present invention provides methods and compositions that can deposit precipitated coatings onto enamel that can be harder than the underlying surface. In this way, the intact tooth structure is altered prior to chemical or physical insult resulting in a tooth more resistant to damage. The present invention provides compositions and methods to demineralize and remineralize teeth to prevent damage to teeth caused by physical and chemical insults. The present invention provides compositions and methods to demineralize and remineralize teeth to prevent damage to teeth caused by physical and chemical insults.

SUMMARY OF THE INVENTION

An oral care composition for demineralization and remineralization of at least one tooth comprising a calcium source, a phosphate source, a fluoride source, wherein the composition is supersaturated relative to fluoroapatite and undersaturated relative to hydroxyapatite, and wherein the pH of the composition is from about 4 to about 8.

An oral care composition for demineralization and remineralization of at least one tooth comprising a calcium source, a phosphate source, a fluoride source, wherein the composition is supersaturated relative to hydroxyapatite and undersaturated relative to all other calcium phosphate crystal phases selected from octacalcium phosphate, tricalcium phosphate, dicalcium phosphate dihydrate, dicalcium phosphate anhydrous, and mixtures thereof, and wherein the pH of the composition is from about 4 to about 8.

An oral care composition for demineralization and remineralization of at least one tooth comprising a calcium source, a phosphate source, a fluoride source, wherein the composition is supersaturated relative to fluoroapatite and undersaturated relative to all other calcium phosphate crystal phases selected from octacalcium phosphate, tricalcium phosphate, dicalcium phosphate dihydrate, dicalcium phosphate anhydrous, and mixtures thereof, and wherein the pH of the composition is from about 4 to about 8.

An oral care composition for demineralization and remineralization of at least one tooth comprising a calcium source, a phosphate source, a fluoride source, a trace metal source, wherein the composition is supersaturated relative to fluoroapatite and undersaturated relative to all other calcium phosphate crystal phases selected from octacalcium phosphate, tricalcium phosphate, dicalcium phosphate dihydrate, dicalcium phosphate anhydrous, and mixtures thereof, and wherein the pH of the composition is from about 4 to about 8.

A method for demineralization and remineralization of at least one tooth comprising contacting at least one tooth with an oral care composition described herein, wherein the contact between at least one tooth and the oral care composition has a treatment time of at least 1 hour.

A method of treatment of at least one tooth comprising contacting at least one tooth with an oral care composition comprising a calcium source, a phosphate source, a fluoride source, wherein the composition is supersaturated relative to fluoroapatite and undersaturated relative to all other calcium phosphate crystal phases selected from octacalcium phosphate, tricalcium phosphate, dicalcium phosphate dihydrate, dicalcium phosphate anhydrous, and mixtures thereof, and wherein the pH of the composition is from about 4 to about 8, wherein the contact between at least one tooth and the oral care composition has a treatment time of at least 1 hour.

A delivery system for remineralization and demineralization of at least one tooth comprising an oral care composition comprising a calcium source, a phosphate source, a fluoride source, wherein the composition is supersaturated relative to fluoroapatite and undersaturated relative to hydroxyapatite, and wherein the pH of the composition is from about 4 to about 8; and a device selected from the group consisting of a tray, a strip, a gel, a foam, a varnish, a slow release device, a lozenge, a retainer, a mouth guard, and mixtures thereof.

DETAILED DESCRIPTION OF THE INVENTION

Figure 1:
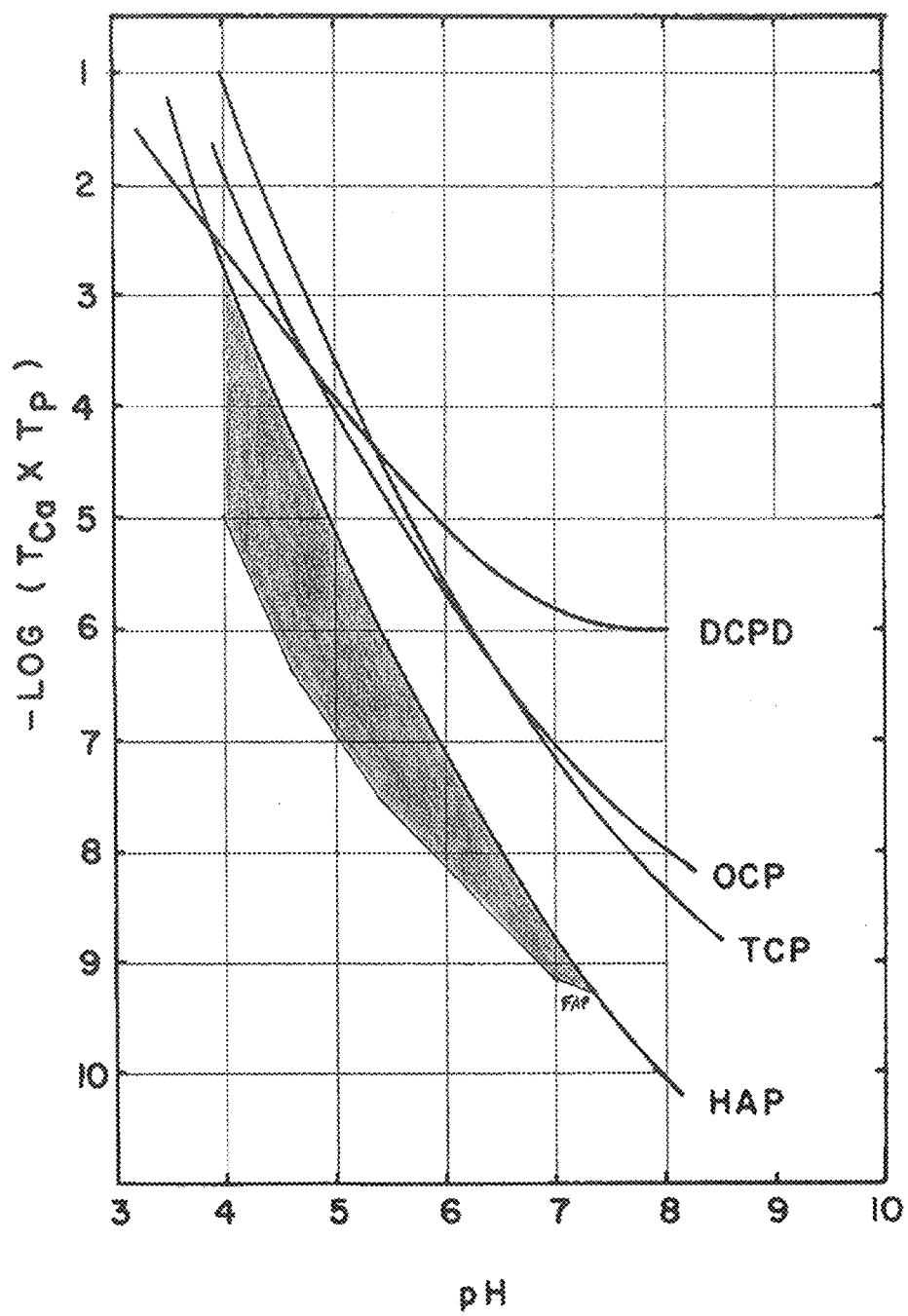
FIG. 1: Solubility isotherms of various calcium phosphate phases at 37° C. and 0.1 mol/L ionic strength. The shaded region represents conditions at 37° C. and 0.1 mol/L ionic strength wherein the composition is supersaturated relative to fluoroapatite and undersaturated relative to hydroxyapatite.

The present invention is directed to the surprising discovery that aqueous compositions with particular concentrations of calcium, phosphate, and fluoride ions can exchange ions from the enamel of teeth. Contact between a tooth and a composition, as disclosed herein, can result in the simultaneous demineralization and remineralization of minerals found in teeth. Additionally, contact between a tooth and a composition, as disclosed herein, can result in the precipitation of a particulate coatings on the enamel surface of teeth.

The present invention is thus based on the surprising discovery that solutions with select concentrations of calcium, phosphate, and fluoride ions can result in the simultaneous demineralization of hydroxyapatite (HAP) and remineralization of fluoroapatite (FAP) on the surface of teeth. Another object of this invention shows the surprising discovery that solutions with select concentrations of calcium, phosphate, and fluoride ions can result in the precipitation of a particulate coating on top of the surface of teeth. Another object of this invention shows the surprising discovery that other metal ions can be incorporated into the enamel layer of teeth. These modifications can result in teeth that are more resistant to the physical and chemical insults commonly introduced to teeth during normal use.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

The foregoing summary is not intended to define every aspect of the invention, and additional aspects are described in other sections, such as the Detailed Description. In addition, the invention includes, as an additional aspect, all embodiments of the invention narrower in scope in any way than the variations defined by specific paragraphs set forth herein. For example, certain aspects of the invention that are described as a genus, and it should be understood that every member of a genus is, individually, an aspect of the invention. Also, aspects described as a genus or selecting a member of a genus should be understood to embrace combinations of two or more members of the genus. With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature.

Features of the compositions and methods are described below. Section headings are for convenience of reading and not intended to be limiting per se. The entire document is intended to be related as a unified disclosure, and it should be understood that all combinations of features described herein are contemplated, even if the combination of features are not found together in the same sentence, or paragraph, or section of this document. It will be understood that any feature of the methods or compounds described herein can be deleted, combined with, or substituted for, in whole or part, any other feature described herein.

All measurements referred to herein are made at 25° C. unless otherwise specified.

The term "orally acceptable carrier" as used herein means a suitable vehicle or ingredient, which can be used to form and/or apply the present compositions to the oral cavity in a safe and effective manner.

Brackets that surround a molecule define the concentration of the target molecule in moles/liter, or M. For example, a reference made to $[Ca^{2+}]$ indicates the concentration of $Ca^{2+}$ in solution in moles/liter unless other units of measurements are specifically mentioned.

The term "saturation," as used herein, refers to the point at which the solvent can dissolve no more of a particular solute and any additional added amounts of the solute will appear as a separate phase. Alternatively, saturation is a point where solute and its constituent ions in solution are at equilibrium. This point is referred to as the solubility product constant for a given solute. Unless otherwise specifically disclosed, saturation is discussed in relative terms according to a solution's $-\log([Ca^{2+}]X[PO_4^{3-}])$ value.

The term "supersaturation," as used herein, refers to a state of solution that contains more of the dissolved material than could be dissolved by the solvent under normal circumstances. Alternatively, supersaturation refers to a solution condition where the ion activity product of constituent ions of a given solute are more than the solubility product constant of the solute, i.e., the ratio of ion activity product of constituent ions to solubility product of solute is greater than one. Unless otherwise specifically disclosed, the term "supersaturation," refers to a solution that contains a higher amount of dissolved calcium and phosphate ions relative to selected solubilized calcium phosphate structures, such as FAP, HAP, TCP, OCP, DCPD, among others at a selected set of experimental conditions, such as pH, temperature, and ionic strength. Unless otherwise specifically disclosed, supersaturation is discussed in relative terms according to a solution's $-\log([Ca^{2+}]X[PO_4^{3-}])$ value.

The term "undersaturation," as used herein, refers to a state of a solution that contains less of a dissolved material than could be dissolved by that quantity of solvent under normal circumstances. Alternatively, undersaturation refers to a solution condition where the ion activity product of constituent ions of a given solute are less than the solubility product constant of the solute, i.e., the ratio of ion activity product of constituent ions to solubility product of solute is less than one. Unless otherwise specifically disclosed, the term "undersaturation," refers to a solution that contains a lower amount of dissolved calcium and phosphate ions relative to selected solubilized calcium phosphate structures, such as FAP, HAP, TCP, OCP, DCPD, among at a selected set of experimental conditions, such as pH, temperature, and ionic strength. Unless otherwise specifically disclosed, undersaturation is discussed in relative terms according to a solution's $--\log([Ca^{2+}]X[PO_4^{3-}])$ value.

The components of the present compositions are described in the following paragraphs.

The present invention lies in the discovery that healthy, intact human hydroxyapatite-mineralized tissues can be further mechanically strengthened through ion exchange thereby simultaneously demineralizing and remineralizing the tissue to yield surfaces that are harder and more resistant to acids. Suitable compositions comprise a calcium source, a phosphate source, a fluoride source, and a trace metal source at a particular ionic strength and pH as described below. Other optional components may be used.

Calcium Source

The calcium source can be any suitable compound comprising calcium. The calcium source can be a water-soluble and/or non-toxic calcium source. The calcium source is water-soluble when at least 0.25 g of the calcium source dissolves in 100 mL of water at 20° C. Alternatively, the calcium source is water-soluble when at least 0.1 g, 0.05 g, and/or 0.01 g of the calcium source dissolves in 100 mL of water at 20° C.

Suitable calcium sources include, but are not limited to, calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, and/or mixtures thereof.

The calcium source and phosphate source can come from the same compound. For example, calcium phosphate dibasic anhydrous can be the source of calcium ions and phosphate ions when dissolved in an aqueous medium.

Phosphate Source

The phosphate source can be any suitable compound comprising phosphate. The phosphate source can be a water-soluble and/or non-toxic phosphate source. A phosphate source is water-soluble when at least 0.25 g of the phosphate source dissolves in 100 mL of water at 20° C. Alternatively, the phosphate source is water-soluble when at least 0.1 g, 0.05 g, and/or 0.01 g of the phosphate source dissolves in 100 mL of water at 20° C.

Suitable phosphate sources include, but are not limited to, alkali salts and ammonium salts of orthophosphoric acid, such as potassium, sodium, or ammonium orthophosphate, monopotassium phosphate, dipotassium phosphate, tripotassium phosphate, monosodium phosphate, disodium phosphate, trisodium phosphate, salts of hydrogen phosphate, and/or mixtures thereof.

As described previously, the calcium source and phosphate source can come from the same compound. For example, calcium phosphate dibasic anhydrous can be the source of calcium ions and phosphate ions when dissolved in an aqueous medium.

Fluoride Source

The fluoride source can be any suitable compound comprising fluoride. The fluoride source can be a water-soluble and/or non-toxic fluoride source. The fluoride source is water-soluble when at least 0.25 g of the fluoride source dissolves in 100 mL of water at 20° C. Alternatively, the fluoride source is water-soluble when at least 0.1 g, 0.05 g, and/or 0.01 g of the fluoride source dissolves in 100 mL of water at 20° C.

Suitable fluoride sources include, but are not limited to, sodium fluoride, potassium fluoride, lithium fluoride, ammonium fluoride, stannous fluoride, stannic fluoride, salts of tetrafluoroborate, salts of fluorophosphates, and/or mixtures thereof.

Halide Source

The halide source can be any suitable compound comprising a non-fluoride halide. The halide source can be a water-soluble and/or non-toxic halide source. The halide source is water-soluble when at least 0.25 g of the carbonate source dissolves in 100 mL of water at 20° C. Alternatively, the halide source is water-soluble when at least 0.1 g, 0.05 g, and/or 0.01 g of the halide source dissolves in 100 mL of water at 20° C.

Suitable halide sources include, but are not limited to, alkali metal halides, alkali earth metal halides, transition metal halides, sodium halides, potassium halides, sodium chloride, sodium bromide, sodium iodide, potassium chloride, potassium bromide, potassium iodide, and/or mixtures thereof.

Trace Metal Source

A trace metal source can be added to incorporate the trace metal into and/or within the hydroxyapatite-mineralized tissues, such as dental enamel. Suitable trace metal sources include compounds with metal ions, such as, but not limited to $Mg^{2+}$, $Sr^{2+}$, $Sn^{2+}$, $Ti^{4+}$, $Zn^{2+}$, $Fe^{2+}$, $Fe^{3+}$, Mo, $B^{3+}$, $Ba^{2+}$, $Ce^{3+}$, $In^{3+}$ and/or mixtures thereof. The trace metal source can be any compound with a suitable metal and any accompanying ligands and/or anions.

Suitable ligands and/or anions that can be paired with trace metal sources include, but are not limited to acetate, ammonium sulfate, benzoate, bromide, borate, carbonate, chloride, citrate, gluconate, glycerophosphate, hydroxide, iodide, oxide, propionate, D-lactate, DL-lactate, orthophosphate, pyrophosphate, sulfate, nitrate, tartrate, and/or mixtures thereof Suitable tin compounds include, but are not limited to stannous acetate, stannous ammonium sulfate, stannous benzoate, stannous bromide, stannous borate, stannous carbonate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, stannous tartrate, and/or mixtures thereof.

Suitable zinc compounds include, but are not limited to zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc propionate, zinc D-lactate, zinc DL-lactate, zinc pyrophosphate, zinc sulfate, zinc nitrate, zinc tartrate, and/or mixtures thereof.

Suitable magnesium compounds include, but are not limited to magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, magnesium tartrate, and/or mixtures thereof.

Suitable strontium compounds include, but are not limited to strontium acetate, strontium ammonium sulfate, strontium benzoate, strontium bromide, strontium borate, strontium caprylate, strontium carbonate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, strontium tartrate, and/or mixtures thereof.

Suitable aluminum compounds include, but are not limited to aluminum acetate, aluminum ammonium sulfate, aluminum benzoate, aluminum bromide, aluminum borate, aluminum carbonate, aluminum chloride, aluminum gluconate, aluminum glycerophosphate, aluminum hydroxide, aluminum iodide, aluminum propionate, aluminum D-lactate, aluminum DL-lactate, aluminum orthophosphate, aluminum pyrophosphate, aluminum sulfate, aluminum nitrate, aluminum tartrate, and/or mixtures thereof.

Suitable iron compounds include, but are not limited to ferrous acetate, ferrous ammonium sulfate, ferrous benzoate, ferrous bromide, ferrous borate, ferrous carbonate, ferrous chloride, ferrous gluconate, ferrous glycerophosphate, ferrous hydroxide, ferrous iodide, ferrous oxide, ferrous propionate, ferrous D-lactate, ferrous DL-lactate, ferrous orthophosphate, ferrous pyrophosphate, ferrous sulfate, ferrous nitrate, ferrous tartrate, and/or mixtures thereof. Additionally, suitable iron compounds include, but are not limited to ferric acetate, ferric ammonium sulfate, ferric benzoate, ferric bromide, ferric borate, ferric carbonate, ferric chloride, ferric gluconate, ferric glycerophosphate, ferric hydroxide, ferric iodide, ferric oxide, ferric propionate, ferric D-lactate, ferric DL-lactate, ferric orthophosphate, ferric pyrophosphate, ferric sulfate, ferric nitrate, ferric tartrate, and/or mixtures thereof.

Suitable barium compounds include, but are not limited to barium acetate, barium ammonium sulfate, barium benzoate, barium bromide, barium borate, barium carbonate, barium chloride, barium gluconate, barium glycerophosphate, barium hydroxide, barium iodide, barium oxide, barium propionate, barium D-lactate, barium DL-lactate, barium orthophosphate, barium pyrophosphate, barium sulfate, barium nitrate, barium tartrate, and/or mixtures thereof.

Suitable cerium compounds include, but are not limited to cerium acetate, cerium ammonium sulfate, cerium benzoate, cerium bromide, cerium borate, cerium carbonate, cerium chloride, cerium gluconate, cerium glycerophosphate, cerium hydroxide, cerium iodide, cerium oxide, cerium propionate, cerium D-lactate, cerium DL-lactate, cerium orthophosphate, cerium pyrophosphate, cerium sulfate, cerium nitrate, cerium tartrate and/or mixtures thereof.

Suitable indium compounds include, but are not limited to indium acetate, indium ammonium sulfate, indium benzoate, indium bromide, indium borate, indium carbonate, indium chloride, indium gluconate, indium glycerophosphate, indium hydroxide, indium iodide, indium oxide, indium propionate, indium D-lactate, indium DL-lactate, indium orthophosphate, indium pyrophosphate, indium sulfate, indium nitrate, indium tartrate and/or mixtures thereof.

pH

The pH of the composition can be from about 4 to about 8. The pH can be from about 4 to about 7.5, from about 4 to about 7, from about 4 to about 6.5, from about 4 to about 6, from about 4 to about 5.5, from about 4 to about 5, from about 4.5 to about 8, from about 5 to about 8, from about 5.5 to about 8, from about 6 to about 8, from about 6.5 to about 8, from about 7 to about 8, or any other suitable range between from about 4 to about 8.

The pH of the composition can be from 4 to 8. The pH can be from 4 to 7.5, from 4 to 7, from 4 to 6.5, from 4 to 6, from 4 to 5.5, from 4 to 5, from 4.5 to 8, from 5 to 8, from 5.5 to 8, from 6 to 8, from 6.5 to 8, from 7 to 8, or any other suitable range between from 4 to 8.

pH adjustment of the composition can be made with any suitable acid, such as, but not limited to hydrochloric acid, or any suitable base, such as, but not limited to sodium hydroxide. Other acids may be used, such as, but not limited to nitric acid, sulfuric acid, and acetic acid. Other bases may be used, such as, but not limited to ammonium hydroxide, potassium hydroxide, and lithium hydroxide.

Ionic Strength

The ionic strength of a solution is a measure of the concentration of ions in that solution. The ionic can be from about 0.01 M to about 1.0 M, from about 0.05 M to about 0.5 M, or from about 0.09 M to about 0.11 M. The ionic strength can be about 0.1 M. The ionic strength can be from 0.01 M to 1.0 M, from 0.05 M to 0.2 M, or from 0.09 M to 0.11 M. The ionic strength can be 0.1 M.

Adjustments to ionic strength can be made using any soluble alkali salt. Adjustments to ionic strength can be made by adding alkali halide salts, such as, but not limited to, lithium chloride, lithium bromide, lithium iodide, sodium chloride, sodium bromide, sodium iodide, potassium chloride, potassium, bromide, potassium iodide, or mixtures thereof.

Optional Components

Other optional components can be included in the composition. These optional components can be added to improve the formulation, aid in delivery of the active ingredients, and/or improve the application experience. The optional ingredients can be included to generate an orally acceptable carrier. Alternatively, the oral care composition can be free of or substantially free of the optional components. The oral care composition can comprise less than about 10%, less than about 5%, less than about 1%, or less than about 0.1%, by weight of the oral care composition, of the optional components.

The composition can be a single-phase or multi-phase system. In a single-phase system, the components are dissolved in a suitable medium. In a multi-phase system, the metal ions and the anions can be in two different phases that can be combined prior to treatment. Alternatively, the two different phases in a multi-phase system can be combined immediately prior to treatment.

The composition can be delivered from any chemically-compatible system whereby the concentration and availability of the calcium, phosphate, and fluoride sources are unaffected by the presence of other optional ingredients.

Other additives in oral care compositions can include, but are not limited to, buffers, abrasives such as silica, alkali metal bicarbonate salts, thickening materials, humectants, water, surfactants, titanium dioxide, flavor system, sweetening agents, xylitol, sugar alcohol, polyols, coloring agents, and mixtures thereof. Examples of such carriers are described in the following paragraphs.

Water

The compositions herein can include at least 5%, at least 10%, at least 20%, at least 50%, at least 75%, at least 90%, or at least 95% by weight of the composition, of water. The water can be USP water.

Water employed in the preparation of commercially suitable oral compositions can be of low ion content and free of organic impurities. In the oral composition, water may comprise from about 1% up to about 99%, from about 5% to about 50%, or from about 25% to about 95%, by weight of the composition herein. The amounts of water include the free water which is added, plus that which is introduced with other materials, such as with sorbitol, silica, surfactant solutions, and/or color solutions.

Abrasive

Compositions of the present invention can include an abrasive. Abrasives may include silica and calcium-based abrasives, such as calcium pyrophosphate, calcium carbonate, dicalcium calcium phosphate, dicalcium phosphate dihydrate, tricalcium phosphate, calcium metaphosphate and beta calcium pyrophosphate. In one embodiment, the abrasive is selected from precipitated silica, polymethylsilsesquioxane silicone resin particles, and mixtures thereof. Alternatively, the oral care composition can be free of or substantially free of an abrasive. The oral care composition can comprise less than about 10%, less than about 5%, less than about 1%, less than about 0.1%, by weight of the oral care composition of an abrasive.

The abrasives useful herein generally have an average particle size ranging between about 0.1 to about 30 microns, and preferably from about 5 to about 15 microns. The abrasive can be precipitated silica or silica gels such as the silica xerogels described in U.S. Pat. Nos. 3,538,230 and 3,862,307. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in U.S. Pat. No. 4,340,583. Other suitable silica abrasives are described in U.S. Pat. Nos. 5,589,160; 5,603,920; 5,651,958; 5,658,553; 5,716,601, and 6,740,311. The abrasive in the oral composition compositions described herein is generally present at a level of from about 5% to about 70% by weight of the composition. Preferably, oral compositions contain from about 10% to about 50% of abrasive, by weight of the oral composition.

Carbonate Source

The composition may include a carbonate source. The carbonate source can be any suitable compound comprising carbonate. The carbonate source can be a water-soluble and/or non-toxic carbonate source. The carbonate source is water-soluble when at least 0.25 g of the carbonate source dissolves in 100 mL of water at 20° C. Alternatively, the carbonate source is water-soluble when at least 0.1 g, 0.05 g, and/or 0.01 g of the carbonate source dissolves in 100 mL of water at 20° C.

Suitable carbonate sources include, but are not limited to, alkali metal carbonate, alkali earth metal carbonate, iron carbonate, zinc carbonate, magnesium carbonate, sodium carbonate, potassium carbonate, and/or mixtures thereof.

Buffering Agent

The present compositions can contain a buffering agent. Buffering agents, as used herein, refer to agents that can be used to adjust the pH of the compositions to a range of about pH 4.0 to about pH 10. The oral composition will typically have a pH of from about 4 to about 8, preferably from about 4.5 to about 6.5, and more preferably from about 5 to about 6.

Suitable buffering agents include alkali metal hydroxides, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Preferred buffers would be those that control the pH in the target range without complexing stannous ions. Preferred buffering agents include acetic acid, sodium acetate, citric acid, sodium citrate, benzoic acid and sodium benzoate. Buffering agents are used at a level of from about 0.1% to about 30%, preferably from about 1% to about 10%, and more preferably from about 1.5% to about 3%, by weight of the present composition.

Additional Carriers

Thickening agents can be used herein, such as those selected from carboxyvinyl polymers, carrageenan, hydroxyethyl cellulose, and water-soluble salts of cellulose ethers such as sodium carboxymethylcellulose and sodium hydroxyethyl cellulose and hydrophobically modified celluloses. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an amount from about 0.1% to about 15%, by weight of the oral composition.

The compositions herein may include from about 0% to 100%, and preferably from about 15% to 55%, by weight of the oral composition, of a humectant. Suitable humectants for use in the invention include glycerin, sorbitol, polyethylene glycol, propylene glycol, xylitol, and other edible polyhydric alcohols.

Surfactants and Sudsing Agents

The compositions herein can also include surfactants, also commonly referred to as sudsing agents. Mixtures of surfactants can be used. Suitable surfactants include anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Many suitable anionic surfactants are disclosed in U.S. Pat. No. 3,959,458. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The nonionic surfactant poloxamer 407 is one of the most preferred surfactant because the poloxamer has been discovered to help reduce the astringency of the stannous. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Many of the suitable nonionic and amphoteric surfactants are disclosed in U.S. Pat. No. 4,051,234. The present composition typically comprises one or more surfactants each at a level of from about 0.25% to about 12%, preferably from about 0.5% to about 8%, and most preferably from about 1% to about 6%, by weight of the composition.

Coloring Agents and Opacifiers

The compositions herein can include from about 0.25% to about 5%, by weight of the composition of titanium dioxide; may contain from about 0.01%, to about 5%, by weight of the composition, of a coloring agent such as one in a 1% aqueous solution.

Flavors, Sensates, and Sweeteners

The compositions herein can include a flavor component. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Sweetening agents and generally used in toothpastes at levels of from about 0.005% to about 5%, by weight of the composition.

Antimicrobial Agents

The present invention can also include other agents to provide antimicrobial benefits. Included among such antimicrobial agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are examplary of typical quaternary ammonium antibacterial agents. Other compounds are bis[4-(R-amino)-1-pyridinium] alkanes as disclosed in U.S. Pat. No. 4,206,215. Also useful are enzymes, including endoglycosidase, papain, dextranase, mutanase, and mixtures thereof. Such agents are disclosed in U.S. Pat. Nos. 2,946,725 and 4,051,234. Specific antimicrobial agents include chlorhexidine, triclosan, triclosan monophosphate, and flavor oils such as thymol. Triclosan and other agents of this type are disclosed in U.S. Pat. Nos. 5,015,466 and 4,894,220. The water insoluble antimicrobial agents, water soluble agents, and enzymes may be present in either the first or second oral compositions if there are two phases. These agents may be present at levels of from about 0.01% to about 1.5%, by weight of the oral composition.

Polyphosphates

Polyphosphates can be included in the compositions herein. The compositions herein may include less than 20%, by weight of the composition, of linear polyphosphates having n+2 or higher. The longer-chain polyphosphate salts include pyrophosphate, tripolyphosphate, tetrapolyphosphate and hexametaphosphate, among others. Polyphosphates larger than tetrapolyphosphate usually occur as amorphous glassy materials. Examples of such polyphosphates are the linear "glassy" polyphosphates having the formula:

wherein X is sodium, potassium or ammonium and n averages from about 6 to about 125. Preferred are polyphosphates manufactured by FMC Corporation (Philadelphia, Pa.) which are commercially known as Sodaphos (n≈6), Hexaphos (n≈13), and Glass H (n≈21). It is also known that polyphosphates with an average chain length greater than about 4 can react with ionic fluoride in oral compositions at ambient temperature and produce monofluorophosphate ions, in addition to altering the pH of the composition. This reaction compromises the efficacy of the oral composition and its ability to provide stable ionic fluoride and polyphosphate to the oral surfaces.

Botanicals

The oral care compositions herein can further comprise at least one botanical or extract thereof selected from chamomile, cinnamon, citrus, clove, echninacea, eucalyptus, fennel, ginger, green tea, hop, magnolia, nutmeg, peppermint, pomegranate, rosemary, saffron, sage, spearmint, star anise, turmeric, wintergreen, extracts thereof and mixtures thereof. A list of botanicals that may be useful herein include those found in U.S. Pat. No. 7,736,629. In one embodiment, the botanical or extract thereof is selected from Hops, extracts thereof and mixtures thereof. Hops are the female seed cones of a hop species, *Humulus lupulus*. Hops are used extensively in brewing for many benefits, including an antibacterial effect that favors the activity of brewer's yeast over less desirable microorganisms. Hops can be subjected to $CO_2$ and ethanol extraction procedures, after which the major components are alpha acids (50-70%), beta acids (20-35%), hop oils (3-7%) and resins (5-15%). One example of a botanical useful herein is the commercially available CLEAN BETA BIO HOPS material from Hopsteiner.

Polyethylene Glycol

The compositions of the present invention may comprise polyethylene glycol (PEG), of various weight percentages of the composition as well as various ranges of average molecular weights. In one aspect of the invention, the compositions have from 0.1% to 15%, preferably from 0.2% to 12%, more preferably from 0.3% to 10%, yet more preferably from 0.5% to 7%, alternatively from 1% to 5%, alternatively from 1% to 4%, alternatively from 1% to 2%, alternatively from 2% to 3%, alternatively from 4% to 5%, or combinations thereof, of PEG by weight of the composition. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula is: $H-(OCH_2CH_2)_u-OH$. One supplier of PEG is Dow Chemical Company (Midland, Mich.) under the brandname of CARBOWAX™.

The oral care compositions herein may include a sweetening agent. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

The compositions herein may include from about 0.001% to about 5%, alternatively from about 0.01% to about 4%, alternatively from about 0.1% to about 3%, alternatively from about 0.5% to about 2%, alternatively 1% to 1.5%, alternatively 0.5% to 1%, alternatively combinations thereof, of a flavorant composition by weight of the composition. The term flavorant composition is used in the broadest sense to include flavor ingredients, or sensates, or sensate agents, or combinations thereof. Flavor ingredients may include those described in U.S. Pat. No. 8,691,190. Excluded from the definition of flavorant composition is "sweetener" (as described above).

Delivery of Compositions

The compositions can be aqueous compositions. The compositions can be continuous phases sufficient to deliver the at least the calcium, phosphate, and fluoride sources to dental enamel.

Delivery of the compositions disclosed herein can be done with any suitable device. A suitable device is any device capable of delivering at least the calcium, phosphate, and fluoride sources to dental enamel for the necessary time to achieve demineralization and remineralization. For example, suitable devices include, but are not limited to, a tray, a strip, a gel, a foam, a varnish, a slow release device, a lozenge, a retainer, a mouth guard, and/or mixtures thereof.

A suitable strip can be used to deliver the compositions disclosed herein. A suitable strip can include a strip comprising materials such as polymers, natural and synthetic wovens, non-wovens, foil, paper, rubber, and/or combinations thereof. The suitable strip can comprising a geling agent, such as a swellable polymer.

The composition should be in contact with the tooth or dental enamel for enough time for the demineralization and remineralization to occur. The composition should be in contact with the tooth or dental enamel for enough time for the tooth or dental enamel to be hardened or possess increased resistance. The treatment time is the time that the composition remains in contact with the tooth. The treatment time can be at least 1 hour, at least 8 hours, at least 12 hours, from about 1 hour to about 16 hours, from about 2 hours to about 16 hours, from about 3 hours to about 14 hours, from about 4 hours to about 13 hours, or any other narrower range. The treatment time is generally longer than the time typically required for dentifrice application or mouth rinse use.

Remineralization and Demineralization

The present invention lies in the discovery that healthy, intact human hydroxyapatite-mineralized tissues can be further mechanically and chemically strengthened through ion exchange thereby demineralizing and remineralizing the tissue to yield surfaces that are harder and more resistant to acids.

The demineralization and remineralization of the tissue can occur simultaneously. Simultaneous demineralization and remineralization can refer to when the processes of demineralization and remineralization occur at some point during the same treatment window. Simultaneous demineralization and remineralization can refer to when the processes of demineralization and remineralization occur at the exact same time or within ten minutes, twenty minutes, thirty minutes, and/or one hour.

The improvement to the strength of dental enamel is caused by exposing healthy, intact tissues to certain compositions with particular concentrations of calcium, phosphate, and fluoride sources.

The exact mineralization behavior of the applied compositions is determined by the concentration of calcium, phosphate, and fluoride.

The concentration of fluoride can be low enough to prevent or limit the formation of $CaF_2$, which can lower the amount of available calcium for the remineralization and demineralization of dental enamel. The concentration of the fluoride source can be less than about 0.05 M, less than about 0.005 M, less than about 0.0045 M, less than about 0.0040 M, less than about 0.0035 M, less than about 0.0030 M, less than about 0.0025 M, less than about 0.0020 M, less than about 0.0015 M, less than about 0.0010 M, and/or less than about 0.0005 M.

The concentrations of calcium and phosphate can be modified to alter the intended effect. For example, when the concentrations of calcium and phosphate are supersaturated relative to the solubility of fluoroapatite (FAP), but undersaturated relative to the solubility of hydroxyapatite (HAP), the simultaneous demineralization of HAP and remineralization of FAP on a tooth can occur. This can result in the net exchange of a hydroxl group ($OH^-$) for a fluoride ($F^-$). This effect can be shown in FIG. 1, which displays a non-limiting example of a range of concentrations disclosed at a particular ionic strength (0.1 M) and temperature (37° C.) that can result in the simultaneous demineralization of HAP and remineralization of FAP on at least one tooth. The shaded area in FIG. 1 can represent the concentrations of calcium and phosphate that are supersaturated relative to FAP and undersaturated relative to HAP at 0.1 M ionic strength and 37° C.

When the concentrations of calcium and phosphate are supersaturated relative to the solubility of HAP, but undersaturated relative to all other calcium phosphate crystal phases, an additional layer of HAP and/or other calcium phosphate minerals can be deposited on the surface of at least one tooth. This effect can be shown in FIG. 2, which displays a non-limiting example of a range of concentrations disclosed at a particular ionic strength (0.1 M) and temperature (37° C.) that can result in the deposition of an HAP and/or other calcium phosphate mineral layer on top of the dental enamel. The shaded area in FIG. 2 can represent the concentrations of calcium and phosphate that are supersaturated relative to FAP and undersaturated relative to all other calcium phosphate crystal phases. TCP is the solubility isotherm for tricalcium phosphate ($Ca_3(PO_4)_2$). OCP is the solubility isotherm for octacalcium phosphate ($Ca_8H_2(PO_4)_6 \cdot H_2O$). DCPD is the solubility isotherm for dicalcium phosphate dihydrate ($CaHPO_4 \cdot H_2O$).

Figure 4:
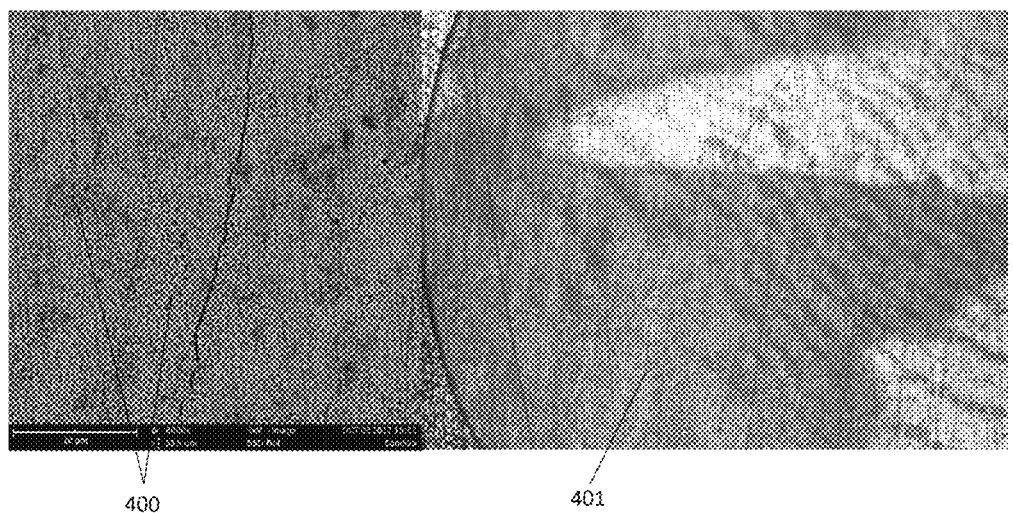
FIG. 4: Scanning electron micrograph (left) and white light micrograph (right) of the precipitated coatings on the enamel surface.

The precipitated coating is visible in FIG. 4. The precipitated coating, is visible either as the rough portions in the scanning electron micrograph, 400, or the dark region, 401, in the otherwise brightly reflective and polished enamel surface in the white light micrograph.

When the concentrations of calcium and phosphate are supersaturated relative to fluoroapatite and undersaturated relative to all other calcium phosphate crystal phases selected from octacalcium phosphate, tricalcium phosphate, dicalcium phosphate dihydrate, dicalcium phosphate anhydrous, and mixtures thereof, the process of demineralization and remineralization and/or the deposition of HAP and/or other calcium phosphate minerals can occur.

When the concentrations of calcium and phosphate are supersaturated relative to octacalcium phosphate and when the negative log of the product of the molar concentration of calcium and phosphate in the medium surrounding the tooth is less than about 2.7 and when the pH is from about 5 to 6, the process of demineralization and/or the deposition of HAP and/or other calcium phosphate minerals can occur.

Trace metal sources can be added to the composition, which can additionally improve the hardening of the tooth and imparting and increase resistance to dietary-like or caries-like acids because of the ability of trace metal ions to inhibit crystal growth and dissolution. The benefits of this ion exchange may be observed in surface hardening, increased mechanical wear resistance, increased acid resistance, micro crack prevention, and/or micro crack repair. Trace metal sources are described above. The concentration of the trace metal source can be greater than about 0.0001 M. The concentration of the trace metal source can be less than about 0.001 M. The concentration of the trace metal source can be from about 0.0001 M to about 0.001 M. Alternatively, the concentration of the trace metal source can be from about 0.00001 M to about 0.01 M, from about 0.000001 M to about 0.1 M, and/or about 0.001 to about 1 M.

Methods

The present invention also relates to methods of demineralization and remineralization of teeth using the compositions disclosed herein. Demineralization and remineralization of teeth can occur simultaneously as described herein. The present invention also relates to methods of precipitating particulate coatings on the enamel surface of teeth. The compositions can be applied using any of the delivery devices described herein under the time limits described herein. The compositions can increase the hardness and acid resistance of dental enamel and/or the tooth. The compositions can increase the resistance to chemical and physical insults typically and occasionally present in the oral cavity.

The present invention also relates to methods of preventing caries using the compositions disclosed herein. Alternatively, the present invention relates to methods of desensitization using the compositions disclosed herein.

The present invention relates to methods of treatment of at least one tooth using the compositions disclosed herein. The treatment can be selected from the group consisting of remineralization and demineralization, prevention of caries, and/or desensitization.

Dentinal hypersensitivity is acute, temporary, localised tooth pain in response to changes in temperature, pressure or chemistry. Exposure of the dentine, often due to recession of the gums, or loss of enamel, frequently leads to hypersensitivity. Dentinal tubules which are open to the surface correlate with hypersensitivity. Dentinal tubules lead from the pulp to the cementum. When the surface cementum of the tooth root is eroded, or exposed by periodontal disease, the tubules become exposed to the external environment and provide a pathway for the passage of fluid to the pulpal nerves. Disclosed herein is a method to desensitize the dentin of teeth. Dentin can be sensitized through the remineralization of enamel using the compositions disclosed herein

EXAMPLES

Generalized Treatment Solution Procedure

All glassware was cleaned with 1% Alconox solution, triple rinsed in tap water, triple rinsed in 1 M-ohm house DI water, and finally triple rinsed in 18.2 M-ohm Millipore water. The glassware dried by air at 20° C. overnight. 450 mL of 18.2 M-ohm Millipore water was placed in a beaker with a stir bar. The calcium source and the phosphate source were added to the beaker with water and the stir bar was activated. For example, in Example 1, the target concentration of calcium phosphate dibasic anhydrous ($CaHPO_4$) was 0.01 M. $CaHPO_4$ served as the calcium source and the phosphate source. Thus, in Example 1, 0.6803 g of $CaHPO_4$ was added to the beaker. In all examples, the solution was cloudy at this point from the undissolved and suspended $CaHPO_4$.

A pH meter (719S Titrino, Metrohm AG, Herisau, Switzerland) was calibrated, according to manufacturer instructions, by testing two solutions with known pHs between pH 3 and pH 7. The pH of the suspended $CaHPO_4$-water system was adjusted slowly by dropwise adding 1M HCl. Sufficient 1M HCl was added to reach the final pH (in Example 1 the target pH was 3). The pH was monitored for 1 hour to ensure stability of the measurement and more 1M HCl was added if the pH changed. The pH was adjusted slowly until the solutions were substantially clear, this process took more than 12 hours depending on how close to the solubility limit of the calcium phosphate dibasic anhydrous the final solution conditions were.

Next, an alkali salt can be added to adjust the final ionic strength of the composition (0.1 M). The target quantity of alkali salt was added while the beaker remained stirring and was allowed to dissolve completely. For example, in Example 1, to achieve a final concentration of 0.01825 M NaCl, 0.5333 g of NaCl was added.

Next, the fluoride source was added slowly, piece-wise so that no $CaF_2$ precipitate formed. For example, in Example 1, to achieve a final concentration of 0.001 M NaF, 0.021 g of NaF was added to the beaker while stirring was conducted.

Next, a trace metal source was added if a trace metal source was actually used in the particular example. For example, in Example 1, to achieve a final concentration of 0.0005 M $MgCl_2$, 0.024 g of $MgCl_2$ was added to the beaker while stirring was conducting.

The pH was adjusted for a final time before treatment. The same approach was used as described previously where the drop-wise addition of 1 M HCl was used to obtain the final pH. As the final pH was reached, the pH was adjusted more finely using 0.1 M HCl. Once the final pH was reached, the solution was transferred to a 500 mL volumetric flask and filled with 18.2 M-Ohm Millipore water until the solution volume was raised to the calibrated line on the volumetric flask.

Enamel samples were obtained from extracted human teeth, substantially free from flesh and debris, by sectioning the enamel from the crown of the chip. The chips were then mounted in an appropriate polymer resin (VersoCit 2 resin, Struers ApS, Ballerup, Denmark) to facilitate their handling. The natural enamel surface or the surface obtained by grinding and polishing the exterior or interior of the enamel can be used. The enamel samples were placed into a plastic container with a tight-fitting lid. Treatment solution in the quantity of 10 mL per enamel sample was transferred to the contained holding the enamel samples. The enamel samples were then incubated at 37° C. for 12 hours to obtain a treated surface. Following 14 hours of incubation, the samples were then examined for changes in their physical properties and in their resistance to caries-like and erosion-like acids.

Changes in Caries Acid Resistance

Increases in acid resistance have been quantified for caries-like acids using a modified version of The Featherstone laboratory pH cycling model with the following modifications to the remineralization and demineralization conditions. See Stookey, G. K. et al. The Featherstone laboratory pH cycling model: a prospective, multi-site validation exercise. *Am. J. Dent.* 24, 322-328 (2011).

Caries free human teeth (erupted third molars, molars, and pre-molars) were inspected under a stereomicroscope (Leica M80, Leica Microsystems Inc., Buffalo Grove, Ill.) on the buccal and lingual surfaces for suitable crack-free windows (about 4×4 mm). Suitable windows were marked with a pencil and these specimens were saved for cutting. Using the Buehler Isomet 1000 saw (Buehler, a division of Illionois Tool Works, Lake Bluff, Ill.), the roots were cut off from each tooth and the crown was cut in half along its mesial-distal axis, which resulted in a buccal and lingual half specimen. Halves with crack-free windows were saved and any remaining tissue was removed by scraping. The enamel surface was lightly abraded, following the shape of the tooth so that the tooth was not ground flat, with 600 grit silicon carbide wet/dry grinding paper (Buehler) for 30 seconds to remove any surface debris or stain. Specimens were placed in an ultra-sonic bath with deionized water (5 min) and then rinsed thoroughly with deionized water.

The specimens were randomly placed into treatment groups. Between 5 and 15 samples were used per group to allow for easy of handling. In one example, 10 samples were used per group. The entire enamel surface, except for one crack-free area measuring approximately 4×4 mm on a flat, clean surface of the enamel, was covered with acid-resistant nail polish. This created an exposed area for testing and the remaining enamel is controlled and not subjected to the cycling process. Windows were washed with a diluted Dawn dishwashing soap and rinsed thoroughly prior to the first treatment.

Each sample in each group of 10 specimens was embedded in Versocit resin leaving the treatment window exposed while forming a resin block around the tooth. During the cycling process, specimens were treated collectively by treatment group and were vertically suspended in the solution so that the enamel is exposed to the designated solution continuously. Specimens were attached to lids of treatment vessels and were stored in a 100% relative humidity, but not in liquid, environment until treatment.

The treatment regimen was a 24-hr period that was repeated for a total of 14 treatment days, five treatment days, followed by two remineralization days when specimens were stored at 37° C. in a remineralizing solution. This procedure was repeated once to reach 14 days.

On the first day of the study (Day) the following procedure was used:
1) Dentifrice slurries (25% paste in water) were prepared by mixing 1 part by weight dentifrice, Crest® Cavity Protection, (10 g) with three parts by volume water (30 ml) into a 50 ml beaker with a cross shaped Teflon coated stir bar. The slurry was mixed on a non-aerating mixer for a minimum of 4 minutes, or until thoroughly mixed, at a speed fast enough to completely disperse the paste but without creating excessive foam. The total volume of the slurry equaled approximately 40 mLs per treatment group (4 mls/tooth specimen). The slurry was then poured into a treatment vessel. The specimens on the lids were then immersed in the slurry for a 1-minute period with occasional hand agitation. The slurries were made fresh just prior to each treatment throughout the cycling process.

2) After the 1-minute dentifrice treatment, the specimens were removed from the slurry and rinsed thoroughly with deionized water to avoid carry-over of fluoride. Dentifrice treatment slurries were discarded. Specimens were then placed in demineralizing solution described below. Each treatment group of 10 specimens was immersed in 400 ml of demineralization solution (40 mL/tooth) in an individual treatment vessel. A designated vessel was used for each treatment group to insure no fluoride cross contamination occured between treatments. All specimens were completely submerged in the solution and placed at 37° C. without stirring for a period of 6 hours. The lids of the vessels were secured to prevent evaporation. The demineralizing solution was reused for the 2-3 days of treatment. A new batch of demineralizing solution was made at the beginning of each 5 day treatment period, as described above.

3) After the 6 hour demineralizing period, the specimen jars were removed from the oven and placed at 20° C. Preparations were then made to initiate a second dentifrice treatment for the day. After slurries were made, the specimen rods were removed from demineralizing solution, rinsed in deionized water, and immersed for 1 minute in the Crest® Cavity Protection dentifrice slurry in a disposable 50 mL conical centrifuge tube (as described in step 1).

4) After the 1 minute dentifrice treatment period, the specimens were rinsed thoroughly with deionized water to remove any excess material from the slurry. Each treatment group of 10 specimens was immersed in 200 ml of remineralization solution (20 mL/tooth). An individual vessel was used for each treatment group to insure no cross contamination occurs between treatments. All specimens were completely submerged in the solution and placed at 37° C. without stirring overnight (18 hrs). Samples attached to the lids of the vessels were sealed to prevent evaporation as described in step 2. The remineralizing solution was reused for the first 2 days of treatment and then refreshed with the remaining solution for the next 2 days. A new batch of remineralizing solution was made on the last day of treatments to be used for the remineralizing period. A fresh batch of solution is prepared again on the beginning of the next treatment period.

Figure 5:
FIG. 5: Series of steps performed for each treatment day.

The series of steps for each treatment day are shown in FIG. 5.

On the afternoon of day 5, following the second dentifrice treatment and deionized water rinse, specimens were placed in a freshly prepared batch of remineralizing solution. Each treatment group of 10 specimens was immersed in 200 ml of remineralization solution (20 mL/tooth). A separate individual vessel was used for each treatment group to insure no cross contamination occurred between treatments. All specimens were completely submerged in the solution, the vessels capped to prevent evaporation, and placed at 37° C. without stirring until the first treatment on Day 8.

The second week of the study began with removing the specimen jars from the 37° C. oven, rinsing with deionized water and beginning the treatment regimen as described on Day 1. The same schedule continued throughout the week concluding with the remineralizing period described previously for the final two days. By the end of the second week, the enamel specimens had been treated for 10 of the total 14 days.

The third week of the study began with the removal of the specimen jars from the 37° C. oven, rinsing with deionized water, and beginning the treatment regimen as described on Day 1. The schedule continued for four additional complete days of cycling/treatments. On the morning of the fifth day on the third week (fifteenth day since treatments began), the specimens were removed from the remineralization solution. By this time, the enamel specimens had been treated for 14 of the required 14 days of cycling. Specimens were rinsed thoroughly with deionized water and the specimens were stored within a sealed vessel under fully saturated, 100% relative humidity (but not under liquid water) conditions until mounting for analysis began.

After 14 days of cycling the 10 specimens from each group were removed from the lids and each specimen was glued to the end of an acrylic rod (cut side down and window facing up) for cross-sectioning through the lesion. Care was taken not to touch the lesion windows. Using the Taylor Hard Tissue Microtome (Series 100 Deluxe, Sci Fab, Lafayette, Colo.), each specimen was then cut in half vertically (crown to root) through the lesion window. Both halves were placed in a 12-well plate and stored under damp conditions. One half was be mounted for analysis, the other half was stored as a back-up if necessary.

All 10 specimens per group were mounted together in a 40 millimeter diameter round block with Versocit cold-set acrylic resin covering all surfaces except the cut face. The mounting was achieved by the following steps:

1) A strip of double-sided tape was placed over a glass plate.
2) An equal size strip of blue painters tape with the sticky side up was placed on top of the double-sided tape.
3) Using the window alignment template, parallel lines were drawn on the tape with pen.
4) Each tooth specimen (cut face down onto the tape) was placed in such a way that the lesion area is parallel to the alignment lines. 10 specimens were placed in one block in rows of 3, 4, 3. Press The teeth were pressed firmly onto the tape, but the lesion window area was avoided.
5) Ring mold was placed around the tooth specimens and was pressed firmly onto the tape.
6) Versocit resin was mixed according to manufacturer instructions. Versocit resin was poured into ring mold covering all tooth specimens.
7) The resin was allowed to set a minimum of 20 minutes. When hardened, the mold was removed from the tape and the resin block was popped out of the mold. Resin blocks were placed with tooth specimens in deionized water overnight to cure.

To permit visualization of the lesion each block was sanded and polished. Sanding and polishing was achieved herein using a Struers Tegramin-30 polisher (Cleveland, Ohio). 600 grit wet/dry sandpaper was used to remove residual resin from the cut face of specimens and then each block was polished serially with 9 um, 3 um and 1 μm DiaPro diamond solution (Struers, Cleveland, Ohio) to a high luster.

Cross-section lesions were indented using the following method. Following polishing, indentations were made with the long axis of the diamond parallel to the outer enamel surface at regular intervals across the lesion and into the underlying sound enamel. A Knoop diamond (Wilson Hardness Tukon 1202, Buehler a division of Illinois Tool Works, Lake Bluff, Ill.) was used under a 10- or 50-gram load. The 10-gram load was used to make the first indent 13 microns from the surface of the tooth. Additional indents were made through the body of the lesion at 13 micron increments yielding a total of 7, 10-gram-load indents in a line. The 50-gram load was used to make indents 25 microns from the last 10-gram-load indent and at 25-micron intervals for a total of 8, 50-gram-load indents in the sound enamel. This process was repeated, such that each sample had two lines of indents to assess the average hardness through the body of the lesion. The Knoop hardness number (KHN) was converted into volume percent mineral (vol % mineral) using Equation 1.

$$(KHN)^{1/2} = 0.197(\text{vol \% mineral}) - 0.24 \quad \text{Equation 1}$$

The vol % mineral lost (mineral loss) was calculated as the area between the total integrated area and the integrated area from the normalized volume percent mineral values from the measurement points. The total integrated area corresponds to the range of the measurement points in units of microns times the average volume percent mineral value determined for the sound enamel region. The area calculation used the trapezoidal rule. The mean mineral loss for the treatment group was obtained by averaging each specimen's mineral loss within a treatment group.

Microscope images were also obtained under reflected brightfield illumination at 5× magnification using a Nikon Optiphot-2 microscope (Nikon, Japan) outfitted with a Moticam 2300 (Motic America, Richmond, British Columbia, Canada) to record digital images. Images were changed to greyscale and adjusted so the pixel lightness range was 0-255. A region of the image (100×250 pixels) through the body of a representative portion of the lesion was converted to vol % mineral by interpolating the lightness value (0 vol % mineral=0 pixel lightness, 87 vol % mineral=255 pixel lightness). Pixel length was calibrated using the lengths of indents obtained during hardness measurements. Lesion profiles were integrated to obtain the mineral loss and compared for each treatment condition.

A demineralizing solution was prepared. The demineralizing solution served as an acid challenge similar to that generated by plaque acids. The following solution was prepared in a 4 L glass beaker:

TABLE 1

Composition of Demineralizing Solution

| Chemical Name | Formula | Molarity | Molecular Weight | Amount in 4 L |
|---|---|---|---|---|
| Glacial acetic acid | $CH_3COOH$ | 75.0 mmol/L | mwt = 60.05 | 17.24 ml |
| Calcium, Phosphate | $CaHPO_4$ | 2.0 mmol/L | mwt = 136.06 | 1.088 g |

Note:
Extra solution was discarded after 7 days.

Glacial acetic acid (17.24 mL) and $CaHPO_4$ (1.088 g) were added to a beaker along with a stir bar and 4 L of 18.2 M-Ohm Millipore water. The composition was stirred until all ingredients were dissolved completely. The pH of the demineralizing solution was adjusted using 50% NaOH to obtain a pH of 4.3 using the pH reading procedure provided above. The demineralizing solution was transferred to and stored in a 4 L volumetric flask. Calcium and Phosphorus levels were confirmed by ICP (Optima 8000, Perkin Elmer, Shelton, Conn.) equaled the theoretical values of 80 ppm Ca and 62 ppm P.

A remineralizing solution was also prepared. The remineralizing solution served as a saliva substitute and had a mineral composition like that found in saliva. The following solution is prepared in a 4 L glass beaker.

TABLE 2

Composition of Remineralizing Solution

| Chemical Name | Formula | Molarity | Molecular Weight | Amount in 4L |
|---|---|---|---|---|
| Calcium Nitrate | $Ca(NO_3)_2 \cdot 4H_2O$ | 0.8 mmol/L | mwt = 236.16 | 0.756 g |
| Potassium Phosphate | $KH_2PO_4$ | 2.4 mmol/L | mwt = 136.09 | 1.307 g |
| Potassium Chloride | KCl | 130.0 mmol/L | mwt = 74.55 | 38.766 g |
| BisTris | $C_8H_{19}NO_5$ | 20.0 mmol/L | mwt = 209.2 | 16.736 g |

Note:
Extra solution was discarded after 7 days.

The remineralization solution was prepared by adding the selected ingredients from Table 2 in the order listed. Calcium nitrate (0.756 g) was added to a 4 L glass beaker with a stir bar and 4 L of water. Once the calcium nitrate was dissolved through stirring with the added stir bar, potassium phosphate (1.307 g) was added and completely dissolved. Next, potassium chloride (38.766 g) was added and dissolved completely. Finally, BisTris ($C_8H_{19}NO_5$, 16.736 g) was added and dissolved completely. This solution was prone to forming precipitates during preparation. If there was any evidence of precipitates, the solution was discarded and made fresh. The pH was adjusted to 7 using the drop-wise addition of 1 M HCl. The pH-adjusted remineralizing solution was transferred to and stored in a 4 L volumetric flask. Calcium and phosphorus levels were confirmed by ICP, as described previously, and equaled the theoretically calculated values of 32 ppm Ca and 74 ppm P.

To assess the increase in acid resistance, enamel specimens were exposed to the treatments listed in the Examples for 14 hours continuously at 35° C. A placebo treatment, wherein the enamel specimens were exposed to (placebo composition) for 14 hours continuously at 35° C. was conducted for comparison.

Following treatment, the enamel specimens were cycled according to the pH cycling method with the remineralizing and demineralization solution modifications above using Crest® Cavity Protection (1100 ppm NaF toothpaste) for three weeks.

Figure 3A:
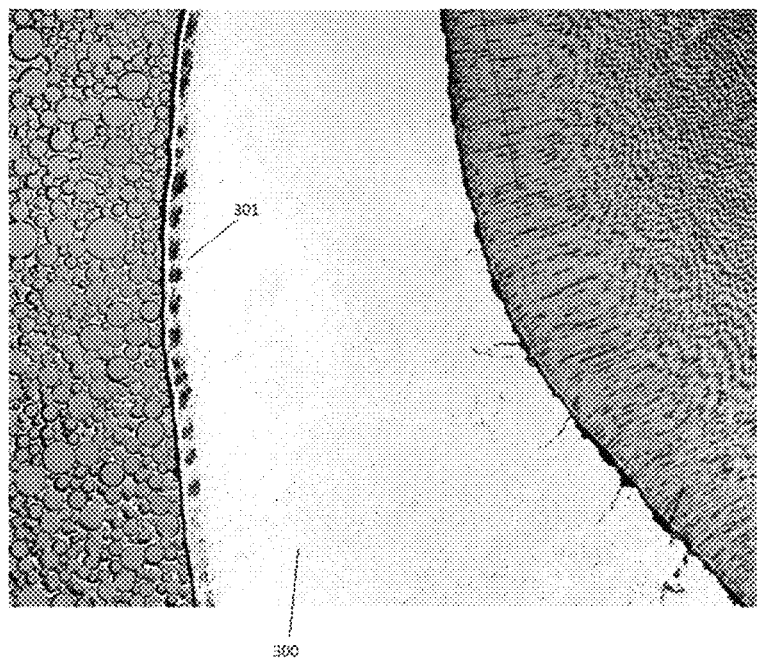
FIGS. 3A and 3B: A comparison in the change in susceptibility of two different teeth to caries-like acids during cycling with Crest® Cavity Protection (CCP) for a placebo pre-treatment (A) and for Example 11 (B).
Figure 3B:
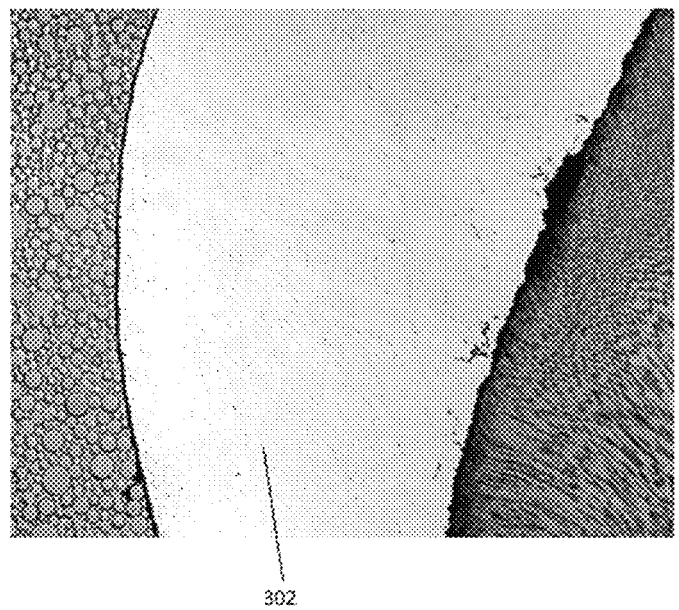

Following treatment, the lesions were additionally assessed by cross-sectional image analysis. FIG. 3 illustrates the difference in susceptibility to acid damage for placebo pretreated and preferred composition pretreated groups using images of the lesion generated during cycling. FIG. 3A shows a cross section of a tooth 300. Lesions, 301, are visible along the left edge of the cross-sectional view of tooth 300. In contrast, a cross-sectional view of a tooth 302 treated with a composition disclosed herein (Example 11) shows no corresponding lesions.

Changes in Dietary Acid Resistance

Increases in acid resistance have also been quantified for dietary-like acids using the in vitro erosion cycling study described by Hooper et al., Journal of Dentistry. 35 (2007), 476-481.

First, specimens were exposed to pre-treatments for 14 hours continuously at 35° C.

Following pre-treatment, they were cycled according to the erosion cycling method for five days where all samples were exposed to Crest® Cavity Protection 1100 ppm NaF dentifrice (The Procter & Gamble Company, Cincinnati, Ohio). The procedure for this erosion cycling study is as follows.

Human enamel specimens were subjected to a 5 day erosion-cycling regimen. Following an initial pellicle formation, specimens were subjected to four treatment sequences per day, one (1) hour apart. The treatment sequences consisted of a dentifrice slurry treatment (1 part dentifrice: 3 parts fresh pooled, human saliva [w:w]), saliva remineralization, and an erosive acid challenge. At the conclusion of the cycling phase, specimens were analyzed using transverse microradiography (TMR) software. The mean surface loss is reported for each treatment group as microns of enamel lost.

Enamel specimens were collected, cut, and mounted in VersoCit-2 resin kit (Struers ApS, Ballerup, Denmark) with the treatment window exposed. Enamel specimens found to have surface imperfections were rejected. Following this preparation, nail polish was applied to approximately ⅔ of the surface, ⅓ on each side leaving the center portion exposed as a treatment window. Specimens were randomly assigned to one of four treatment groups (approximately 5 specimens/group).

The evening before the treatment phase began; each group of specimens was placed into 20 ml of fresh, pooled human saliva to initiate the formation of a pellicle layer on the enamel surfaces. To begin the treatment phase, dentifrice slurries were prepared by mixing 5 grams of dentifrice with 15 grams of fresh, pooled human saliva for a period of not less than 4 nor more than 5 minutes prior to use. Fresh slurry was prepared for each treatment. Each treatment cycle consisted of: dentifrice slurry (1 min) then rinse in deionized water then saliva (5 min) then erosion challenge (10 min) then rinse in deionized water. There were 4 treatments each day and five treatment days. Dentifrice treatments consisted of immersing the specimens into the dentifrice slurry for one minute while rotating at 75 rpm. The erosion challenge consisted of soaking each treatment group in 20 ml of 1% citric acid. A fresh volume of citric acid was used for each treatment cycle. Saliva was refreshed after every treatment cycle. Any time specimens were not in treatment, they remained in 20 ml of pooled, human saliva (stirred). At night, each group of specimens remained immersed in saliva (stirred at room temperature).

After 5 days of treatment, specimens were rinsed well in deionized water and stored refrigerated in a humid environment until analysis. In order to begin the analysis phase, a layer of nail polish was applied to the entire surface of each specimen to seal the surface and protect the fragile eroded areas. Specimens were cut plano-parallel using a hard tissue sectioning saw perpendicularly through the eroded portion of the sample and across the eroded area. Each section was cut to allow the control and treated portion to be represented for analysis. A thin section (100 microns) was removed from each specimen and placed flat on a specially designed holder that fits into a camera mounted to an X-ray generator. These sections were then exposed to CuKα radiation. Radiographs were taken using Kodak 50253 Holographic film. The film was processed using standard black and white film developing methods. Radiographic images were then analyzed using transmission microradiography (TMR), a computer based image analysis system (Inspektor Research Systems BV, Amsterdam, The Netherlands). By comparing the original surface, based on the control (untreated) area, to the post treatment surface, the depth of the eroded area was measured (microns of mineral lost).

To assess changes in dietary acid resistance, samples treated according to the example compositions below were compared to a placebo treatment in the erosion cycling study where all treatments received Crest® Cavity Protection toothpaste according to the instructions above.

Enamel Hardness

Increases in enamel hardness were assessed using surface microhardness measurements and a Vickers diamond (Wilson Hardness Tukon 1202, Buehler a division of Illinois Tool Works, Lake Bluff, Ill.) applied using 50 g for 10 s following solution treatment. The effectiveness of the treatment was determined by comparing the hardness to a water-treated control group. Indent size was measured and converted into a Vickers Hardness Number.

Measuring the hardness on the natural surface of teeth is challenging. It is necessary to find a surface sufficiently flat and perpendicular to the objective and indenter as to be accurately measured. Measurements were only recorded if the indent appeared square, thus verifying that the measurement location was planar perpendicular to both the objective and indenter. Three measurements were made per surface (tooth) and averaged together. The effectiveness of the treatment was assessed by averaging hardness differences across ten teeth for a given treatment composition.

Data

Example 1

| | |
|---|---|
| Magnesium Chloride, Anhydrous (mol/L) | 0.0005 |
| Calcium Phosphate, Dibasic, Anhydrous (mol/L) | 0.01 |
| Sodium Fluoride, Anhydrous (mol/L) | 0.001 |
| Sodium Chloride, Anhydrous (mol/L) | 0.01825 |
| $-\log_{10}([Ca] \times [PO4])$ | 4.00 |
| Ionic Strength (mol/L) | 0.100 |
| pH (adjustment with 1.0M HCl) | 3.00 |
| % Hardness increase vs. Untreated Control | −61 |

Example 2

| | |
|---|---|
| Magnesium Chloride, Anhydrous (mol/L) | 0.0005 |
| Calcium Phosphate, Dibasic, Anhydrous (mol/L) | 0.0001 |
| Sodium Fluoride, Anhydrous (mol/L) | 0.001 |
| Sodium Chloride, Anhydrous (mol/L) | 0.04795 |
| $-\log_{10}([Ca] \times [PO4])$ | 8.00 |
| Ionic Strength (mol/L) | 0.100 |
| pH (adjustment with 1.0M HCl) | 4.00 |
| % Hardness increase vs. Untreated Control | −35 |

Example 3

| | |
|---|---|
| Magnesium Chloride, Anhydrous (mol/L) | 0.0005 |
| Calcium Phosphate, Dibasic, Anhydrous (mol/L) | 0.001 |
| Sodium Fluoride, Anhydrous (mol/L) | 0.001 |
| Sodium Chloride, Anhydrous (mol/L) | 0.4554 |
| $-\log_{10}([Ca] \times [PO4])$ | 6.00 |
| Ionic Strength (mol/L) | 0.101 |
| pH (adjustment with 1.0M HCl) | 5.00 |
| % Hardness increase vs. Untreated Control | +10 |

Example 4

| | |
|---|---|
| Magnesium Chloride, Anhydrous (mol/L) | 0.0005 |
| Calcium Phosphate, Dibasic, Anhydrous (mol/L) | 0.00315 |
| Sodium Fluoride, Anhydrous (mol/L) | 0.001 |
| Sodium Chloride, Anhydrous (mol/L) | 0.0388 |

-continued

| | |
|---|---|
| $-\log_{10}([Ca] \times [PO4])$ | 5.00 |
| Ionic Strength (mol/L) | 0.100 |
| pH (adjustment with 1.0M HCl) | 4.55 |
| % Hardness increase vs. Untreated Control | +50 |

Example 5

| | |
|---|---|
| Magnesium Chloride, Anhydrous (mol/L) | 0.0005 |
| Calcium Phosphate, Dibasic, Anhydrous (mol/L) | 0.000316 |
| Sodium Fluoride, Anhydrous (mol/L) | 0.001 |
| Sodium Chloride, Anhydrous (mol/L) | 0.04730 |
| $-\log_{10}([Ca] \times [PO4])$ | 7.00 |
| Ionic Strength (mol/L) | 0.100 |
| pH (adjustment with 1.0M HCl) | 5.50 |
| % Hardness increase vs. Untreated Control | +11 |

Example 6

| | |
|---|---|
| Magnesium Chloride, Anhydrous (mol/L) | 0.0005 |
| Calcium Phosphate, Dibasic, Anhydrous (mol/L) | 0.0100 |
| Sodium Fluoride, Anhydrous (mol/L) | 0.001 |
| Sodium Chloride, Anhydrous (mol/L) | 0.0182 |
| $-\log_{10}([Ca] \times [PO4])$ | 4.00 |
| Ionic Strength (mol/L) | 0.100 |
| pH (adjustment with 1.0M HCl) | 4.10 |
| % Hardness increase vs. Untreated Control | +1.3 |

Example 7

| | |
|---|---|
| Magnesium Chloride, Anhydrous (mol/L) | 0.0005 |
| Calcium Phosphate, Dibasic, Anhydrous (mol/L) | 0.00178 |
| Sodium Fluoride, Anhydrous (mol/L) | 0.001 |
| Sodium Chloride, Anhydrous (mol/L) | 0.0429 |
| $-\log_{10}([Ca] \times [PO4])$ | 5.50 |
| Ionic Strength (mol/L) | 0.100 |
| pH (adjustment with 1.0M HCl) | 3.40 |
| % Hardness increase vs. Untreated Control | −69 |

Example 8

| | |
|---|---|
| Magnesium Chloride, Anhydrous (mol/L) | 0.0005 |
| Calcium Phosphate, Dibasic, Anhydrous (mol/L) | 0.00178 |
| Sodium Fluoride, Anhydrous (mol/L) | 0.001 |
| Sodium Chloride, Anhydrous (mol/L) | 0.0429 |
| $-\log_{10}([Ca] \times [PO4])$ | 5.50 |
| Ionic Strength (mol/L) | 0.100 |
| pH (adjustment with 1.0 M HCl) | 4.00 |
| % Hardness increase vs. Untreated Control | −16 |

Example 9

| | |
|---|---|
| Magnesium Chloride, Anhydrous (mol/L) | 0.0005 |
| Calcium Phosphate, Dibasic, Anhydrous (mol/L) | 0.0178 |
| Sodium Fluoride, Anhydrous (mol/L) | 0.001 |
| Sodium Chloride, Anhydrous (mol/L) | 0 |

-continued

| | |
|---|---|
| $-\log_{10}([Ca] \times [PO4])$ | 3.50 |
| Ionic Strength (mol/L) | 0.100 |
| pH (adjustment with 1.0 M HCl) | 3.40 |
| % Hardness increase vs. Untreated Control | −1.2 |

Example 10

| | |
|---|---|
| Stannous Fluoride (mol/L) | 0.001 |
| Calcium Phosphate, Dibasic, Anhydrous (mol/L) | 0.001 |
| Sodium Chloride, Anhydrous (mol/L) | 0.046 |
| Sodium Gluconate (mol/L) | 0.001 |
| $-\log_{10}([Ca] \times [PO4])$ | 6.00 |
| Ionic Strength (mol/L) | 0.100 |
| pH (adjustment with 1.0 M HCl) | 5.00 |
| % Hardness increase vs. Untreated Control | +34 |
| Increased acid resistance? | Yes |

Example 11

| | |
|---|---|
| Magnesium Chloride, Anhydrous (mol/L) | 0.001 |
| Calcium Phosphate, Dibasic, Anhydrous (mol/L) | 0.001 |
| Sodium Fluoride, Anhydrous (mol/L) | 0.001 |
| Sodium Chloride, Anhydrous (mol/L) | 0.046 |
| $-\log_{10}([Ca] \times [PO4])$ | 6.00 |
| Ionic Strength (mol/L) | 0.100 |
| pH (adjustment with 1.0 M HCl) | 5.00 |
| % Hardness increase vs. Untreated Control | +41 |
| Increased acid resistance? | Yes |

Example 12

| | |
|---|---|
| Strontium Chloride, Hexahydrate (mol/L) | 0.001 |
| Calcium Phosphate, Dibasic, Anhydrous (mol/L) | 0.001 |
| Sodium Fluoride, Anhydrous (mol/L) | 0.001 |
| Sodium Chloride, Anhydrous (mol/L) | 0.046 |
| $-\log_{10}([Ca] \times [PO4])$ | 6.00 |
| Ionic Strength (mol/L) | 0.100 |
| pH (adjustment with 1.0 M HCl) | 5.00 |
| % Hardness increase vs. Untreated Control | +43 |
| Increased acid resistance? | Yes |

Example 13

| | |
|---|---|
| Ferrous Sulfate, Heptahydrate (mol/L) | 0.001 |
| Calcium Phosphate, Dibasic, Anhydrous (mol/L) | 0.001 |
| Sodium Fluoride, Anhydrous (mol/L) | 0.001 |
| Sodium Chloride, Anhydrous (mol/L) | 0.046 |
| $-\log_{10}([Ca] \times [PO4])$ | 6.00 |
| Ionic Strength (mol/L) | 0.100 |
| pH (adjustment with 1.0 M HCl) | 5.00 |
| % Hardness increase vs. Untreated Control | +45 |
| Increased acid resistance? | Yes |

Example 14

| | |
|---|---|
| Zinc Chloride, Anhydrous (mol/L) | 0.001 |
| Calcium Phosphate, Dibasic, Anhydrous (mol/L) | 0.001 |
| Sodium Fluoride, Anhydrous (mol/L) | 0.001 |

-continued

| | |
|---|---|
| Sodium Chloride, Anhydrous (mol/L) | 0.046 |
| $-\log_{10}([Ca] \times [PO4])$ | 6.00 |
| Ionic Strength (mol/L) | 0.100 |
| pH (adjustment with 1.0 M HCl) | 5.00 |
| % Hardness increase vs. Untreated Control | +52 |
| Increased acid resistance? | Yes |

Example 15

| | |
|---|---|
| Ferric Sulfate, Hydrate (mol/L) | 0.001 |
| Calcium Phosphate, Dibasic, Anhydrous (mol/L) | 0.001 |
| Sodium Fluoride, Anhydrous (mol/L) | 0.001 |
| Sodium Chloride, Anhydrous (mol/L) | 0.046 |
| $-\log_{10}([Ca] \times [PO4])$ | 6.00 |
| Ionic Strength (mol/L) | 0.100 |
| pH (adjustment with 1.0 M HCl) | 5.00 |
| % Hardness increase vs. Untreated Control | −23 |
| Increased acid resistance? | No |

Example 16

| | |
|---|---|
| Aluminum Sulfate, Hydrate (mol/L) | 0.001 |
| Calcium Phosphate, Dibasic, Anhydrous (mol/L) | 0.001 |
| Sodium Fluoride, Anhydrous (mol/L) | 0.001 |
| Sodium Chloride, Anhydrous (mol/L) | 0.046 |
| $-\log_{10}([Ca] \times [PO4])$ | 6.00 |
| Ionic Strength (mol/L) | 0.100 |
| pH (adjustment with 1.0 M HCl) | 5.00 |
| % Hardness increase vs. Untreated Control | −4 |
| Increased acid resistance? | Yes |

Example 17

| | |
|---|---|
| Calcium Phosphate, Dibasic, Anhydrous (mol/L) | 0.001 |
| Sodium Fluoride, Anhydrous (mol/L) | 0.001 |
| Sodium Chloride, Anhydrous (mol/L) | 0.046 |
| $-\log_{10}([Ca] \times [PO4])$ | 6.00 |
| Ionic Strength (mol/L) | 0.100 |
| pH (adjustment with 1.0 M HCl) | 5.00 |
| % Hardness increase vs. Untreated Control | +41 |
| Increased acid resistance? | Yes |

Example 18

| | |
|---|---|
| Magnesium Chloride, Anhydrous (mol/L) | 0.0005 |
| Calcium Phosphate, Dibasic, Anhydrous (mol/L) | 0.01 |
| Sodium Fluoride, Anhydrous (mol/L) | 0.001 |
| Sodium Chloride, Anhydrous (mol/L) | 0.01825 |
| $-\log_{10}([Ca] \times [PO4])$ | 4.00 |
| Ionic Strength (mol/L) | 0.100 |
| pH (adjustment with 1.0 M HCl) | 4.75 |
| Precipitate coating on teeth | Yes |
| % Hardness increase vs. Untreated Control | +51 |

Example 19

| | |
|---|---|
| Magnesium Chloride, Anhydrous (mol/L) | 0.0005 |
| Calcium Phosphate, Dibasic, Anhydrous (mol/L) | 0.00177 |
| Sodium Fluoride, Anhydrous (mol/L) | 0.001 |
| Sodium Chloride, Anhydrous (mol/L) | 0.04294 |
| $-\log_{10}([Ca] \times [PO4])$ | 5.50 |
| Ionic Strength (mol/L) | 0.100 |
| pH (adjustment with 1.0 M HCl) | 5.50 |
| Precipitate coating on teeth | Yes |
| % Hardness increase vs. Untreated Control | +55 |

Example 20

| | |
|---|---|
| Magnesium Chloride, Anhydrous (mol/L) | 0.0005 |
| Calcium Phosphate, Dibasic, Anhydrous (mol/L) | 0.000316 |
| Sodium Fluoride, Anhydrous (mol/L) | 0.001 |
| Sodium Chloride, Anhydrous (mol/L) | 0.04730 |
| $-\log_{10}([Ca] \times [PO4])$ | 7.00 |
| Ionic Strength (mol/L) | 0.100 |
| pH (adjustment with 1.0 M HCl) | 6.50 |
| Precipitate coating on teeth | Yes |
| % Hardness increase vs. Untreated Control | +18 |

TABLE 3

Erosion Acid Resistance and Caries Acid Resistance

| Treatment | Erosion Cycling Depth Lower is Better (μm, n = 5) | Caries Cycling Mineral Loss Lower is Better (vol % mineral − μm, n = 5) |
|---|---|---|
| Water Only for Comparison | 31 ± 11 | 950 ± 870 |
| Example 10 | 29 ± 3.1 | 96 ± 103 |
| Example 11 | 32 ± 6.9 | −24 ± 33 |
| Example 12 | 28 ± 3.8 | 38 ± 99 |
| Example 13 | 24 ± 4.0 | 60 ± 87 |
| Example 14 | 33 ± 6.5 | 1.0 ± 1.1 |
| Example 15 | 43 ± 7.4 | 2000 ± 660 |
| Example 16 | 24 ± 7.4 | 310 ± 230 |
| Example 17 | 32 ± 2.0 | −7.5 ± 21 |

TABLE 4

% Hardness Increase

Figure 2:
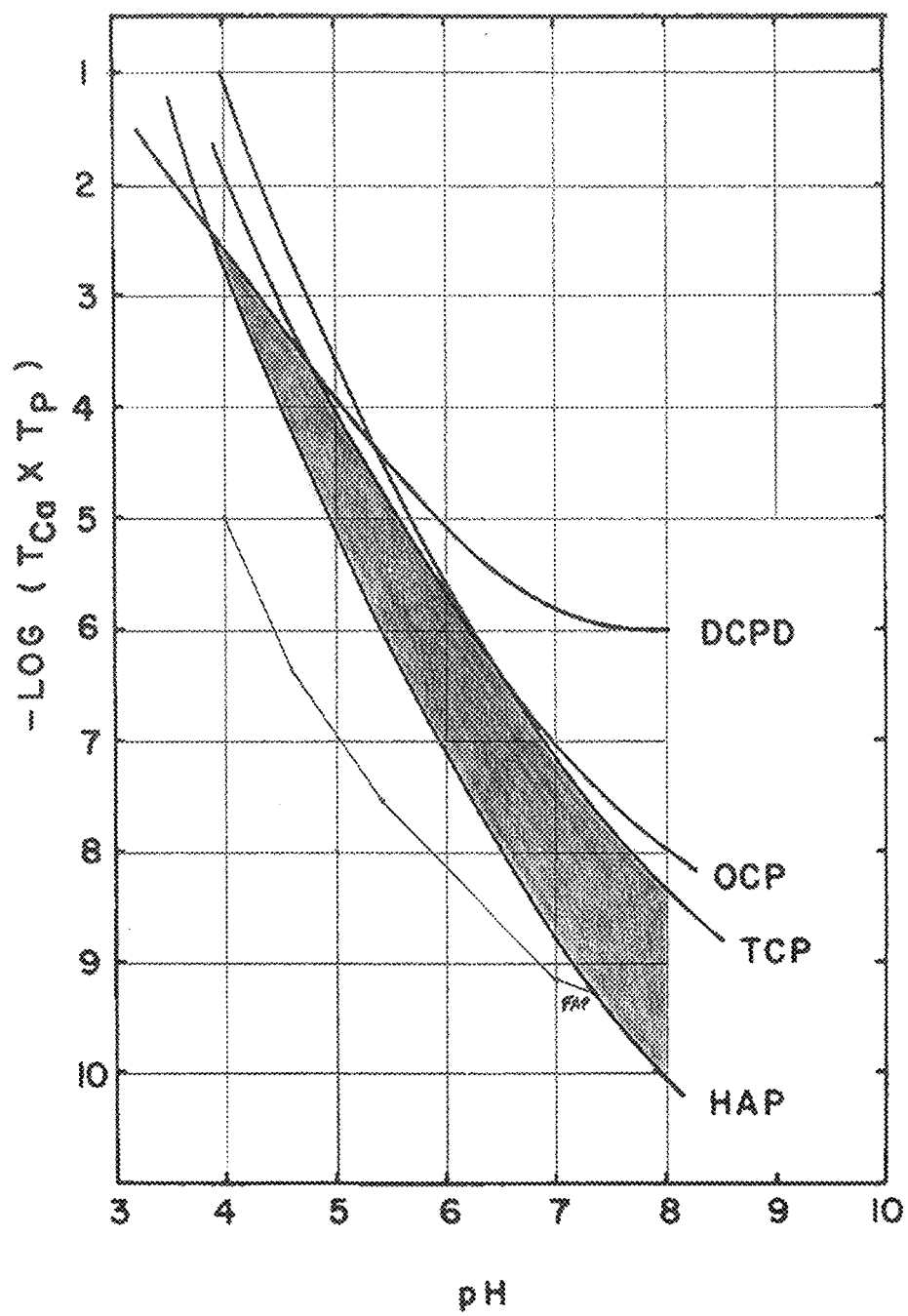
FIG. 2: Solubility isotherms of calcium phosphate phases at 37° C. and 0.1 mol/L ionic strength. The shaded region represents conditions at 37° C. and 0.1 mol/L ionic strength wherein the composition is supersaturated relative to hydroxyapatite and undersaturated relative to all other calcium phosphate crystal phases.

| Treatment | Trace Metal Source | Shaded Region | % Hardness Increase vs Untreated Control |
|---|---|---|---|
| Example 1 | $Mg^{2+}$ | None | −61 |
| Example 2 | $Mg^{2+}$ | None | −35 |
| Example 3 | $Mg^{2+}$ | FIG. 1 | 10 |
| Example 4 | $Mg^{2+}$ | FIG. 1 | 50 |
| Example 5 | $Mg^{2+}$ | FIG. 1 | 11 |
| Example 6 | $Mg^{2+}$ | FIG. 1 | 1.3 |
| Example 7 | $Mg^{2+}$ | None | −69 |
| Example 8 | $Mg^{2+}$ | None | −16 |
| Example 9 | $Mg^{2+}$ | None | −1.2 |
| Example 10 | $Sn^{2+}$ | FIG. 1 | 34 |
| Example 11 | $Mg^{2+}$ | FIG. 1 | 41 |
| Example 12 | $Sr^{2+}$ | FIG. 1 | 43 |
| Example 13 | $Fe^{2+}$ | FIG. 1 | 45 |
| Example 14 | $Zn^{2+}$ | FIG. 1 | 52 |
| Example 15 | $Fe^{3+}$ | FIG. 1 | −23 |
| Example 16 | $Al^{3+}$ | FIG. 2 | −4 |
| Example 17 | — | FIG. 2 | 41 |

TABLE 4-continued

% Hardness Increase

| Treatment | Trace Metal Source | Shaded Region | % Hardness Increase vs Untreated Control |
|---|---|---|---|
| Example 18 | $Mg^{2+}$ | FIG. 2 | 51 |
| Example 19 | $Mg^{2+}$ | FIG. 2 | 55 |
| Example 20 | $Mg^{2+}$ | FIG. 2 | 18 |

Table 3 shows the erosion resistance and caries acid resistance for examples 10-17 and a control sample treated with water. Samples with a lower erosion cycling depth had an improved erosion resistance. Examples 10, 12, 13, and 16 had lower values for erosion cycling depth than the comparative water sample. Examples 10 ($Sn^{2+}$), 12 ($Sr^{2+}$), 13 ($Fe^{2+}$), and 16 ($Al^{3+}$) contained trace metal sources which were found to be helpful for lowering the value for erosion cycling depth. Example 17 did not contain any trace metal source. Examples 11 ($Mg^{2+}$), 14 ($Zn^{2+}$), and 15 ($Fe^{3+}$), did contain trace metal sources, which indicated that these ions were not helpful for increasing erosion resistance. Examples 10-14, 16, and 17 all had lower values of mineral loss after caries cycling.

Table 3 also shows the caries acid resistance of Examples 10-17 compared with a water control. Samples with a lower amount of mineral loss were more resistant to caries acid. Only example 15 ($Fe^{3+}$) demonstrated a worse caries cycling mineral loss than the water control. All other samples demonstrated a much lower amount of mineral loss.

Table 4 demonstrates the % hardness increase compared with an untreated control. Examples 1, 2, 7, 8, and 9 all demonstrated a negative % hardness increase, which indicated they were softer than the untreated sample. Examples 3-6 and 10-14 are represented by the shaded region in FIG. 1. Unexpectedly, Examples 3-6 and 10-14 demonstrated an increased hardness compared with an untreated sample despite being only slightly different in the values for the $-\log([Ca^{2+}] \times [PO_4^{3-}])$ as shown in FIG. 1. Example 15 did not show an increased hardness, despite being in the same shaded region of FIG. 1, because it utilized $Fe^{3+}$ as a trace metal source. Other trace metal sources, such as $Sn^{2+}$, $Sr^{2+}$, $Fe^{2+}$, or $Zn^{2+}$ improved the hardness of the samples.

Additionally, Examples 17-20 are represented by the shaded region in FIG. 2. Unexpectedly, Examples 17-20 demonstrated an increase in hardness compared with an untreated sample despite being only slightly different in the values for the $\log([Ca^{2+}] \times [PO_4^{3-}])$ as shown in FIG. 2. Example 16 did not show an increased hardness, despite being in the same shaded region of FIG. 2, because it utilized $Al^{3+}$. Having no trace metal source, such as in Example 17, or having $Mg^{2+}$, such as in Examples 18-20, were shown to improve the hardness of the samples.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A single aqueous oral care composition for simultaneous demineralization and remineralization of at least one tooth comprising:
   a calcium source;
   a phosphate source;
   a fluoride source;
   at least 75%, by weight of the oral care composition, of water;
   wherein the composition is supersaturated relative to fluoroapatite and undersaturated relative to all calcium phosphate crystal phases selected from octacalcium phosphate, tricalcium phosphate, dicalcium phosphate dihydrate, dicalcium phosphate anhydrous, and mixtures thereof; and;
   wherein the pH of the composition is from about 4 to about 8.

2. The composition of claim 1, wherein the fluoride source comprises a concentration of fluoride of less than about 100 ppm.

3. The composition of claim 1, further comprising a trace metal source, the trace metal source comprising a magnesium ion, a strontium ion, a tin ion, a titanium ion, a zinc ion, a ferrous ion, a molybdenum ion, boron ion, a barium ion, a cerium ion, or mixtures thereof.

4. The composition of claim 3, wherein the concentration of the trace metal source is from about 0.000001 M to about 0.1 M.

5. The composition of claim 1, wherein the fluoride source is NaF, KF, LiF, $NH_4F$, $SnF_2$, $SnF_4$, $BF_4^-$, monofluorophosphate, or mixtures thereof.

6. The composition of claim 1, wherein the calcium source comprises calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, or mixtures thereof.

7. The composition of claim 1, wherein the phosphate source comprises alkali and ammonium salts of orthophosphoric acid, monopotassium phosphate, dipotassium phosphate, tripotassium phosphate, monosodium phosphate, disodium phosphate, trisodium phosphate, or mixtures thereof.

8. The composition of claim 1, wherein the composition is supersaturated relative to hydroxyapatite and fluoroapatite.

9. The composition of claim 1, wherein the composition is undersaturated relative to hydroxyapatite.

10. A single aqueous oral care composition for simultaneous demineralization and remineralization of at least one tooth comprising:
    a calcium source;
    a phosphate source;
    a fluoride source;
    at least 75%, by weight of the oral care composition, of water;

wherein the composition is supersaturated relative to fluoroapatite and undersaturated relative to hydroxyapatite; and;

wherein the pH of the composition is from about 4 to about 8.

11. The composition of claim 10, wherein the fluoride source comprises a concentration of fluoride of less than about 100 ppm.

12. The composition of claim 10, further comprising a trace metal source, the trace metal source comprising a magnesium ion, a strontium ion, a tin ion, a titanium ion, a zinc ion, a ferrous ion, a molybdenum ion, boron ion, a barium ion, a cerium ion, or mixtures thereof.

13. The composition of claim 12, wherein the concentration of the trace metal source is from about 0.000001 M to about 0.1 M.

14. The composition of claim 10, wherein the fluoride source comprises NaF, KF, LiF, $NH_4F$, $SnF_2$, $SnF_4$, $BF_4^-$, monofluorophosphate, or mixtures thereof.

15. The composition of claim 10, wherein the calcium source comprises calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, or mixtures thereof.

16. The composition of claim 10, wherein the phosphate source comprises alkali and ammonium salts of orthophosphoric acid, monopotassium phosphate, dipotassium phosphate, tripotassium phosphate, monosodium phosphate, disodium phosphate, trisodium phosphate, or mixtures thereof.

* * * * *